United States Patent [19]

Korth et al.

[11] Patent Number: 5,520,636
[45] Date of Patent: May 28, 1996

[54] APPARATUS FOR FLUSHING THE URINARY BLADDER

[75] Inventors: Knut Korth, Merzhausen; Erich Becker, Bad Krozingen, both of Germany

[73] Assignee: KNF-Neuberger, Freiburg-Munzingen, Germany

[21] Appl. No.: 182,651

[22] Filed: Jan. 18, 1994

Related U.S. Application Data

[63] Continuation-in-part of Ser. No. 953,764, Sep. 30, 1992, abandoned, which is a continuation of Ser. No. 734,562, Jul. 23, 1991, abandoned.

[30] Foreign Application Priority Data

Aug. 3, 1990 [DE] Germany ............... 40 24 676.0

[51] Int. Cl.$^6$ ................................... A61M 1/00
[52] U.S. Cl. ................................... 604/30
[58] Field of Search ................ 604/30, 27, 32, 604/35, 50, 48, 66, 65, 67, 247, 249, 246; 137/505.41

[56] References Cited

U.S. PATENT DOCUMENTS

| | | | |
|---|---|---|---|
| 2,359,111 | 9/1944 | Hughes | 137/505.4 |
| 2,930,378 | 3/1960 | Buyers | 128/350 |
| 3,185,153 | 5/1965 | Leucci | 128/227 |
| 3,481,334 | 12/1969 | Diskin et al. | 128/230 |
| 3,570,488 | 3/1971 | Diskin et al. | 128/230 |
| 3,604,419 | 9/1971 | Haifa et al. | |
| 3,730,209 | 5/1973 | Binard et al. | 137/217 |
| 3,900,022 | 8/1975 | Widran | 128/7 |
| 4,132,227 | 1/1979 | Ibe | 128/4 |
| 4,231,366 | 11/1980 | Schael | 128/214 E |
| 4,306,557 | 12/1981 | North | |
| 4,419,094 | 12/1983 | Patel | 604/93 |
| 4,508,533 | 4/1985 | Abramson | 604/35 |
| 4,516,968 | 5/1985 | Marshall et al. | 604/174 |
| 4,573,965 | 3/1986 | Russo | 604/30 |

FOREIGN PATENT DOCUMENTS

| | | | |
|---|---|---|---|
| 3540326 | 5/1987 | Germany . | |
| 3805709 | 9/1989 | Germany . | |
| 641964 | 3/1984 | Switzerland . | |
| 2185689 | 7/1987 | United Kingdom . | |
| 0673280 | 7/1979 | U.S.S.R. | 604/30 |

Primary Examiner—Gene Mancene
Assistant Examiner—Jeffrey A. Smith
Attorney, Agent, or Firm—Walter C. Farley

[57] ABSTRACT

A device for flushing the urinary bladder (1) has an instrument inserted from the outside into the inside of the bladder and a feed line (17a, 17b, 10) from a supply receptacle (16) feeding pressurized flushing liquid and a drain line (11, 15) to a drain. The interior bladder fluid pressure is regulated by a pressure regulator connected through the feed line to the bladder. The regulator is held at constant height. The pressure regulator has a valve (31, 32) controlling the flow cross-section which is in turn controlled by the pressure sensor (27) located on the side of the valve facing the bladder and ascertaining the pressure in the feed line (17b, 10). The feed conduit between the regulator and the bladder has a constant flow resistance smaller than the minimum possible flow resistance of the drain conduit multiplied by a maximum pressure variation $P_{Fmax}$ and divided by a maximum allowable bladder pressure $P_{Bmax}$.

12 Claims, 2 Drawing Sheets

APPARATUS FOR FLUSHING THE URINARY BLADDER

CROSS-REFERENCE TO RELATED APPLICATIONS

This is a continuation-in-part of application Ser. No. 07/953,764 filed Sep. 30, 1992, now abandoned, which was a continuation of Ser. No. 07/734,562 filed Jul. 23, 1991, now abandoned.

FIELD OF THE INVENTION

This invention relates to an apparatus for flushing the bladder of a patient, the apparatus having a feed line and a drain line and means for regulating the pressure of the flushing liquid within the bladder.

BACKGROUND OF THE INVENTION

A number of purposes can be served by flushing the urinary bladder such as post-surgical treatment following surgery inside the bladder, i.e., at the prostate. As a rule, the instrument placed in the bladder is a flexible catheter, typically a balloon catheter device which admits a constantly flowing flushing liquid into the bladder and then drains it.

Flushing also is used during cutting surgical intervention inside the bladder, for instance at the bladder wall. The instrument introduced into the bladder then is a rigid endoscope with optics and a cutting device, typically a high-frequency driven loop. In this case, flushing serves to create a clear field of view by washing away blood and cut-off tissue pieces from the field of view.

The flushing of the urinary bladder can be carried out using a variety of instruments such as a two-duct catheter or a two-duct endoscope. However, intervention using two instruments placed separately into the bladder also is possible, one typically being inserted through the urethra and the other being put in place by means of a suprapubic trocar directly through the skin into the bladder. In the latter case one of the two ducts required for flushing may be present in one of the instruments and the other in the second instrument. Alternatively, both ducts may be present in one instrument put in place supra-pubically.

Care always must be taken during flushing that the bladder is filled in the same manner as much as possible. If the pressure inside the bladder is too low, it will collapse. This can be dangerous, especially during surgery inside the bladder, because then the rear bladder wall suddenly drops onto the instrument and can be injured.

On the other hand, excessive bladder pressure is undesirable. During flushing there are always fresh cut wounds in the bladder through which the patient's blood circulation is open to the bladder. If the bladder pressure is excessive, the flushing liquid can enter the patient's blood stream which can lead to the so-called TUR syndrome (transurethral resection syndrome). The TUR syndrome is dangerous and must be avoided under any circumstance. When surgery is being performed on a tumor, excessive pressure also creates the dangerous possibility of washing tumor cells into the patient's bloodstream.

Excessive bladder pressure is also a drawback in post-surgery flushing. Scars over freshly operated bladder sites may tear open because of excessive pressure, thereby delaying wound healing.

Besides methods of continuous flushing in which a supply line continuously feeds liquid and a drain line continuously evacuates it, there are also intermittent flushing methods requiring only one duct alternatingly serving as feed and as drain duct. Again, care must be taken to see that, when the liquid is introduced, the maximum bladder pressure is not exceeded, and then that the bladder is emptied in due time and filled again.

The desired bladder pressure is in the order of a few tens of centimeters of water head. Typically, the pressure is controlled by valves in the feed or the drainage. The surgeon optically watches the bladder filling, that is, he views the inside of the bladder through the endoscope optics. Manually actuated valves allow him to control the bladder pressure.

Although exceedingly costly, electronically controlled pumps are known to regulate the bladder pressure in devices of the above mentioned type and such pumps assure equality of feed and drain flows at all times. While the bladder volume is thereby kept constant, the pressure is not. Externally created effects tending to raise the pressure, i.e., from causes outside of the flushing system such as external pressure on the bladder or respiratory pressure changes, lead to increases in pressure that this control means cannot handle.

German patent document 35 40 326 C2 discloses a device of the kind having inlet and outlet ducts. In addition to the ducts required for feed and drainage, this design also provides a measurement duct in the instrument by which the bladder pressure is applied to a pressure sensor. The inside bladder pressure measured in this manner controls a pump in the drain line, so that a constant pressure can be maintained inside the bladder.

This design incurs the drawback of substantial additional complexity entailed by the pressure control. This complexity follows from the need to provide a pump in the drain line, and moreover this pump must be a precision pump. Again, the instrument requires a measurement duct in addition to the ducts already present, so that complete redesign is necessary, creating significant problems in finding the necessary space in view of the well-known, exceedingly restricted spatial conditions in which such instruments must be used.

German Offenlegungsschrift 38 05 709 discloses a flushing device similar to the previously mentioned one. In this case an overflow is present in the drain line that keeps the bladder pressure constantly at the static pressure level resulting from the height difference between bladder and overflow. However, the bladder pressure is monitored in the drain line which inherently is always in danger of being clogged. It may be blocked by the tissue pieces released in bladder surgery. Therefore, this design is usable only when using a suprapubic trocar as the drain line and selecting conduits with suitably large cross-sections to prevent any clogging. As regards instruments which must receive both feed and drain lines and therefore can make available only very narrow cross-sections, the use of such designs are precluded. They clearly entail the drawback of additional surgical intervention and difficult handling.

The prior art also includes U.S. Pat. No. 3,900,022, Widran, which has a flushing system. However, Widran includes various control valves and other instruments in the flow path between a pressure regulator and the bladder. As a result, the flow path between the regulator and the bladder includes pressure drops of variable and unknown magnitudes such that the pressure which is registered at the regulator cannot be relied upon as being directly related in any known fashion to the pressure in the bladder.

SUMMARY OF THE INVENTION

An object of the present invention is to provide a device for washing the bladder using inlet and outlet ducts or tubes for a flushing liquid while maintaining constant pressure in the bladder, which is economical and which allows automatic bladder-pressure control with high reliability and with easy handling.

Briefly described, the invention comprises an apparatus for flushing the urinary bladder of a patient while maintaining the pressure within the bladder within a selected range of pressures below a maximum allowed pressure $P_{Bmax}$ and with maximum pressure variation $P_{Fmax}$ induced by flow variations. An instrument insertable from the outside into the inside of a patient's bladder provides a feed conduit and a drain conduit, each conduit having an opening at the distal end thereof to be positioned within the bladder and an outside proximal end. A supply receptacle provides flushing liquid under pressure. A bladder pressure regulator has an input connected to the supply receptacle and an output connected to the proximal end of the feed conduit for providing flushing liquid at an adjustable constant pressure. The feed conduit between the regulator and the bladder has a constant flow resistance smaller than the minimum possible flow resistance of the drain conduit multiplied by the maximum pressure variation $P_{Fmax}$ and divided by the maximum allowable pressure $P_{Bmax}$. The regulator is mounted at a constant height relative to the bladder to be flushed, not higher than a minimum acceptable pressure within the bladder.

The device of the invention has a pressure regulator in the feed line. This provides the inherent advantage that the feed line is continuously kept clear by the inflowing flushing liquid and thus cannot clog. As a result, the pressure sensor of the pressure regulator always detects the pressure in the bladder. Essentially, the pressure detected by the sensor agrees with the pressure in the bladder because the dynamic pressure drop is negligible for the small required flushing flow rates, of the magnitude of a few ml/min, even where there are narrow ducts. However, the static pressure resulting from the height difference between the pressure regulator and the bladder must be included. Therefore the pressure regulator must be fixed in height in a suitable manner.

The pressure regulator can be a simple valve controlling the flushing flow, the valve being actuated by a pressure sensor located on the side of the valve which faces the bladder. As described below, such a pressure regulator may be designed in a simple manner to be maintenance-free and, with appropriate adjustment means, allows simple pressure adjustment to the desired level. The pressure regulator operates entirely independently of any clogging of the drain line. If this drain line were fully clogged, the pressure regulator would shut the valve and maintain the pressure in the bladder at the preset level. It is particularly important that the pressure regulator maintains the pressure in the bladder constant regardless of the magnitude of the flushing flow. The magnitude of the flushing flow can be selected in some other way, for instance by suitable control of the drain flow. The pressure regulator is applicable to all flushing methods, especially to continuous, permanent flushing.

Because the construction of the invention simultaneously uses the feed duct as a measurement duct, any conventional instrument may be used. The pressure regulator provided by the invention offers substantial cost advantages relative to the known suction pump driven by a pressure sensor. Therefore the invention allows very economical pressure regulation.

Attaching the pressure sensor in the feed line separate from the pressure measuring instrument is advantageous. In that way the pressure sensor can be retrofitted as an accessory for known pressure measuring instruments. Illustratively, the sensor may be connected in the tube leading to the instrument.

The feature of using a sensor which is a spring-urged membrane exposed on one side to the flowing liquid and on the other side to ambient air is also advantageous. Because of its simple mechanical design, such a membrane pressure regulator can be economically manufactured and is suitable for long-term, reliable, finely controlled pressure regulation. The membrane may be spring-loaded by its own elasticity or using additional springs.

The feature of using a valve having a circular seat and a conical valve head surface is also advantageous. The conical surface of the valve head together with the rim of the valve aperture provides a circular line seal of high quality. Moreover the conical surface makes the valve self-centering every time it closes, so that the valve unit and the membrane are always self-centered by play in the valve. As a result, no additional centering means are required.

Employing a separate spring on the air side of the membrane is also advantageous. A higher control pressure may be set by means of the spring, and the use of a membrane which is not self-returning is possible also. The spring is mounted in the air space and hence need not be sterilized and is sheltered from corrosion which might otherwise be caused by the flushing liquid.

Using an externally adjustable system for setting the spring force allows the bladder pressure to be finely controlled by means of the adjustment device.

It is desirable to use an actuation means which, after overcoming play, acts on the valve unit in the direction of opening. This actuation means permits manually opening the valve when it is first being used to permit the liquid to enter and to purge air from the regulator so that it will not interfere with subsequent use.

By making the housing parts of the pressure regulator out of plastic, the pressure regulator is simplified and made more economical and can be made with easily sterilized surfaces or may also be produced as a disposable item. The pressure regulator must be sterilized or replaced before each use because it is located in the feed line.

Inserting a flow meter in the feed line allows one to monitor the flow of flushing liquid independently of watching the bladder pressure. This is especially important in the regulation of bladder pressure because it allows detecting changes in the flow of flushing liquid. Therefore the separate display of flow is advantageous.

BRIEF DESCRIPTION OF THE DRAWINGS

The invention is shown illustratively and schematically in the drawings wherein.

DESCRIPTION OF THE PREFERRED EMBODIMENTS

Figure 1:
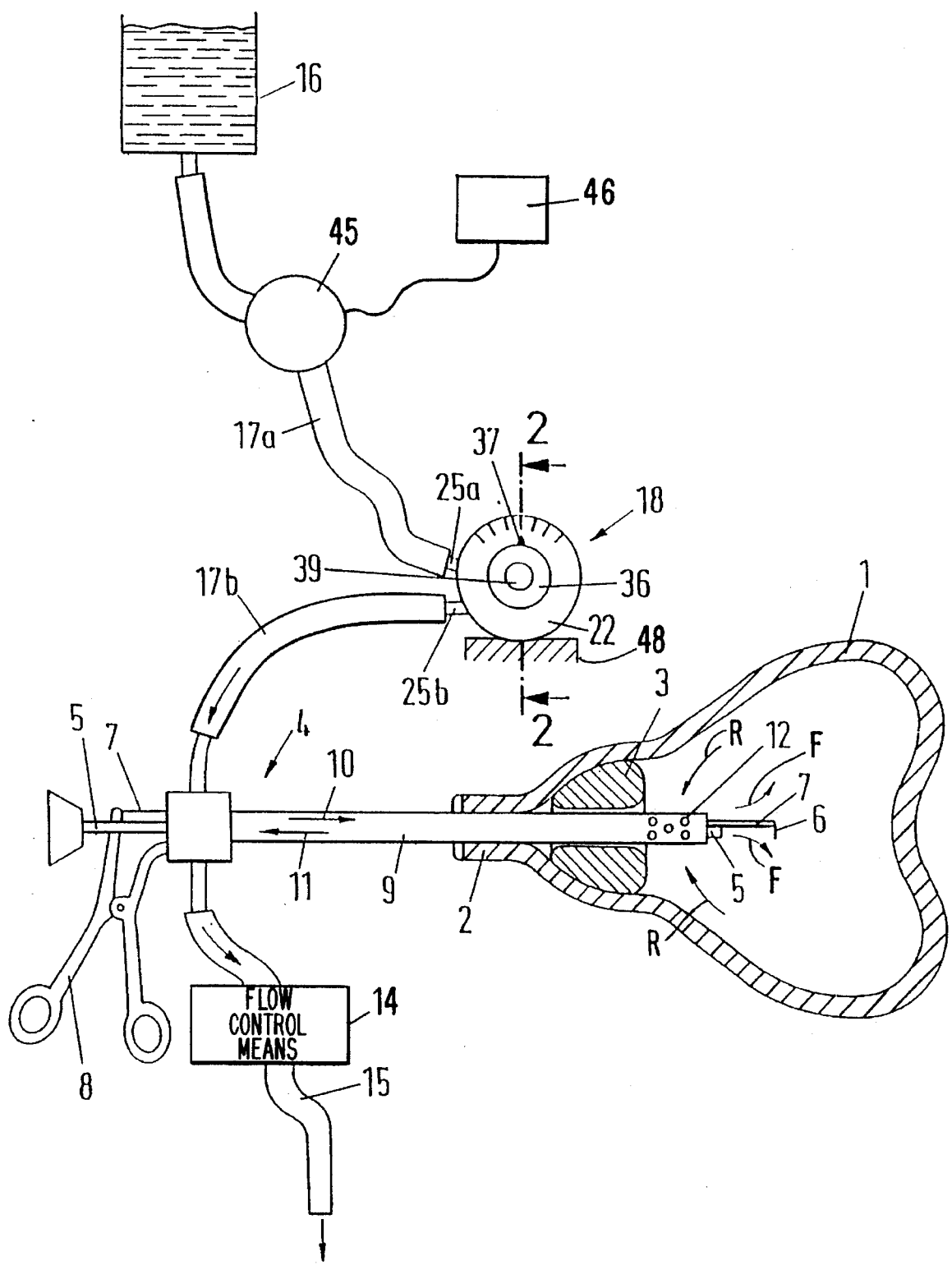
FIG. 1 is a schematic of a flushing device of the invention with a resectoscope in a bladder, shown sectionally, and with the pressure regulator of FIG. 2.

FIG. 1 is a sectional view of a bladder 1, namely a human urinary bladder. It further shows the transition to the urethra 2 enclosed in part by the prostate 3.

A resectoscope indicated generally at 4 is inserted into the bladder, preferably an endoscope of a type widely used in urology with viewing optics 5 and with a high-frequency driven cutting loop 6 on a loop support 7 of which the proximal end can be actuated in the axial direction by a scissor handle 8.

The optics 5 and the loop support 7 are mounted inside an enclosing shaft 9 suitably divided in the longitudinal direction into a feed duct 10 and a drain duct 11 schematically indicated by arrows in FIG. 1. As shown by the flow arrows in FIG. 1, the feed duct 10 is axially open at the distal end of the shaft 9 and accordingly the flushing liquid discharges therefrom in the direction of the arrows F into the bladder. The drain duct 11 is open at the distal end of the shaft 9 through external holes 12 entered by the flushing liquid moving out of the bladder in the shown direction of the arrows R.

A flow controller 14 is connected in the drain tube 15 which passes from the proximal end of shaft 9 to a discharge receiving means, not shown. Controller 14 is used to control the drain flow which establishes the total flow volume of the flushing system and can be a valve installed as shown in conduit 15 or elsewhere along the drain path, or a suction pump can be used.

Normally, the flow resistance of the drain conduit is quite high, typically because channel 11 within the instrument is narrow or because the passage somewhere between openings 12 and the discharge from tube 15 is clogged with tissue. In this circumstance, which is quite normal, flow through the bladder would be too small to accomplish the desired flushing. It is therefore desirable to use a suction pump rather than simply a valve as controller 14, and the pump can be regulated to establish a desired level of flow.

Flushing liquid flows from a supply receptacle 16 to the proximal end of inflow passage 10 and this receptacle is normally suspended at an elevated location relative to the patient's bladder to thereby provide the required flushing pressure. The supply receptacle 16 is connected by a succession of feed tubes 17a, 17b and a pressure regulator indicated generally at 18 is inserted in series between these two tube segments and supported at a fixed height by means schematically indicated at 48.

By means of the shown resectoscope 4, the surgeon can look through the optics 5 into the inside of the bladder and, after moving the instrument into a desired operating position, he may cut by moving the cutting loop 6 to-and-fro, to remove, for example, carcinoma from the mucous membrane cladding the bladder or planing the prostate 3 from the inside.

Strong bleeding is produced thereby and tissue particles very likely will be floating inside the bladder. A steady flushing flow in the direction of the arrows shown inside the bladder assures maintaining a clear field of view through the optics 5.

Care must be taken to assure that the interior bladder pressure remain constant, so that the bladder is always be unfolded to maintain a fully "inflated" shape such as that shown. With adequate pressure, the bladder is unfolded enough so that all its parts are accessible and enough working room is in it for operating. Yet the pressure must not be high enough to force the flushing liquid into the blood vessels at the bleeding sites, as discussed above.

It is important that the pressure not change abruptly. If the pressure were to drop markedly, the rear bladder wall might be forced toward the instrument and there might be unwanted contact with the cutting loop 6, whereby injury or even cutting through the bladder wall might ensue.

Therefore the shown pressure regulator 18 assures highly accurate preservation of the bladder pressure.

Figure 2:
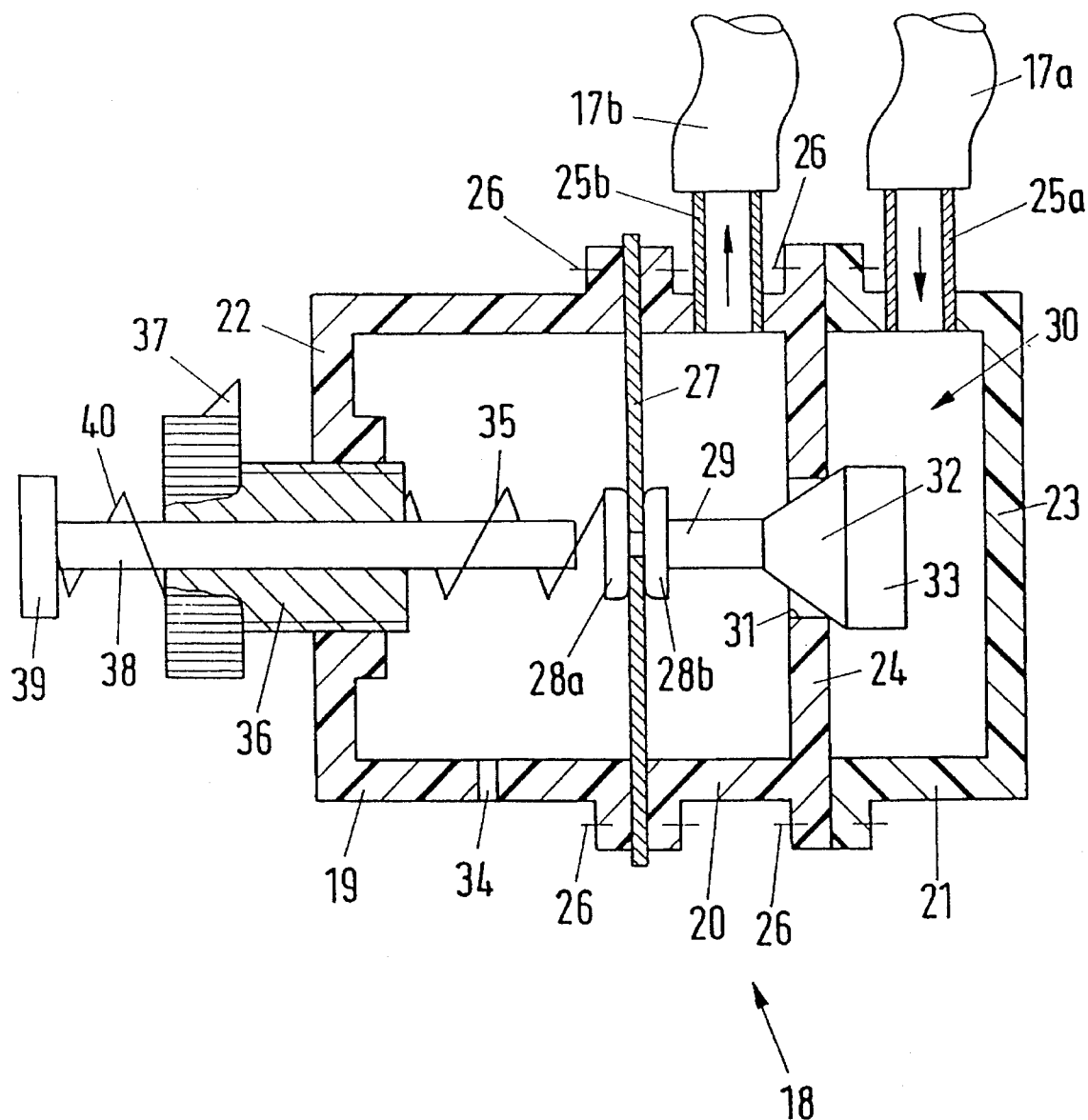
FIG. 2 is a longitudinal section along line 2—2 of FIG. 1 of the pressure regulator.

FIG. 2 shows the pressure regulator along the section of line 2—2 of FIG. 1. In the shown embodiment of FIG. 1, the pressure regulator is circular in axial view. It comprises an air chamber housing 19, a drain chamber housing 20 and a feed chamber housing 21. Each housing has a cylindrical housing wall, all three housings being of the same diameter, and also each has a transverse wall. The transverse wall of the air chamber housing 19 forms the control-side end wall 22 of the pressure regulator and the transverse wall of the feed chamber housing 21 forms its rear wall 23. The transverse wall of the drain chamber housing 20 forms a partition 24 between the drain and the feed chambers. The drain tube 17b is connected to the drain chamber in the drain chamber housing 20. The feed tube 17a from the supply receptacle 17a is connected by suitable connection stubs 25a, 25b to the feed chamber in the feed chamber housing 21.

In the embodiment shown, the housing parts 19, 20 and 21 are formed with flanges which abut one another and are held together in a sealing relationship by fastening means schematically indicated by dashes 26, for instance being screwed, bonded, clamped or joined together in some other way.

An elastic membrane 27 is clamped between the air chamber housing 19 and the drain chamber housing 20 at their flange connection and serves to separate the chambers within those housing parts from each other. A valve rod 29 of a valve unit indicated generally at 30 is attached by means of suitable retaining disks 28a, 28b to the center of membrane 27. Rod 29 is attached to a valve head 33 which extends through a valve aperture 31 in partition 24 from the feed chamber in the feed chamber housing 21. Head 33 has a conical valve surface 32 which faces toward the membrane, i.e., the smaller end of the conical surface is closest to the membrane, the smaller cross-section being smaller than the diameter of opening 31 and the larger cross-section at the other end being larger than that of the circular valve aperture 31 so that the edge of opening 31 forms a valve seat.

The air chamber in the air chamber housing 19 opens through a vent aperture 34 to the atmosphere. A helical compression spring 35 in the air chamber is mounted with its axis along the axis of the valve rod 29, one end of the spring resting against one side of the membrane 27 and the other end of the spring abutting the inner end of an adjustment screw 36 which is threaded into an internally threaded opening through end wall 22 in the axial direction of the valve rod 29. The return force of the membrane 27 can be finely controlled by rotation of adjustment screw 36. The position so set can be monitored by means of a pointer 37 on the adjustment screw 36 relative to a scale on the end wall 22 (FIG. 1).

A pushrod 38 passes axially through a central passage through the adjustment screw 36 and can be pushed inward by a knob 39 against the force of a helical compression spring 40 extending between the knob 39 and the adjustment screw 36, the inner end of rod 38 normally resting a small distance from disk 28a. As knob 39 is pushed, after overcoming a small amount of lost motion due to the gap between the end of the rod and disk 28a (FIG. 2), the membrane 27 is moved in the direction which opens the valve 31, 32 (that is, in FIG. 2, to the right).

What we would like to achieve is a system in which, by adjusting the pressure regulator, the operator can adjust the pressure within the bladder, and in which, once that adjustment has been made, the bladder pressure will remain constant under all circumstances while the operator is working within the bladder.

The pressure regulator produces a constant pressure at the proximal (upper) end of feed conduit 17b to which it is connected. This constant pressure at the proximal end of the feed conduit does not correspond exactly to the pressure within the bladder. The pressure $P_B$ within the bladder can be expressed as follows (all pressures being considered gauge pressures):

$$P_B = P_R - P_F + P_W \tag{1}$$

wherein $P_B$ is the actual pressure within the bladder, $P_R$ is the adjusted, constant pressure at the output of the pressure regulator and at the proximal end of conduit 17b, $P_F$ is the pressure drop through the feed conduit 17b, 10 resulting from fluid flow, and $P_W$ is the pressure of the water head which is equal to the height of the water column between the bladder and the regulator. The pressure regulator must be held at a constant height above the bladder during flushing in order to avoid pressure variations. $P_W$ can be treated as a constant because we hold the regulator at a constant height. Since the regulator is adjusted to a pressure at which the bladder assumes a desired shape, it is not important that we know what the numerical value of the bladder pressure is and this constant can therefore be considered added to the constant pressure at the output of the regulator and will be omitted from the following discussion.

It can be seen from equation (1) that the pressure within the bladder is the sum of a constant pressure at the regulator and the pressure drop $P_F$ through the feed conduit. $P_F$ is variable and therefore leads to undesirable variations which are to be avoided.

$P_F$ is the product of flow resistance and flow rate and can be expressed as $$P_F = R_f * F \tag{2}$$

wherein $R_f$ is the flow resistance of the feed conduit, and

F is the flow rate of fluid through the conduit.

Expression (2) shows that when flow is zero, $P_F$ is zero and when flow is maximum, $P_F$ is maximum. The instrument is designed so that the feed conduit has no variable means such as valves, etc., which means that $R_F$ is constant. No clogging in the feed conduit can occur because in the feed conduit only clear water flows. Thus, F is the remaining variable which can lead to variations in $P_F$.

We cannot control F. It varies because the drain conduit, which is in series with the feed conduit and therefore has the same flow rate and volume, is subject to clogging. If we use an uncontrolled simple pump in the drain conduit, the flow can change. If there is a flow control valve in the drain conduit by which the operator can adjust the flow rate, this can also introduce flow variation.

To overcome this problem, we want to guarantee to the operator a system in which the pressure within the bladder is kept nearly constant, once the pressure has been adjusted to a certain level, and that this pressure does not vary more than a narrow tolerance range, e.g., 5%. Having recognized that the only variable is $P_F$, the aim is to keep that variable under a maximum which can be called $P_{Fmax}$. From (2), it is clear that $P_{Fmax}$ occurs when flow is at a maximum, $F_{max}$, i.e., $$P_{Fmax} = R_f * F_{max} \tag{3}$$

The next step is to determine $F_{max}$. The instrument is designed so that the flow resistance $R_f$ of the feed conduit is smaller than the flow resistance $R_d$ of the drain conduit. The flow through the entire instrument and bladder, F, can be calculated from the drain conduit. At the inner (upper) end of drain conduit 15 the pressure is $P_B$, the bladder pressure and at the outer end the pressure is zero, ambient pressure. As in (2)

$$P_B = R_d * F, \text{ or}$$

$$F = P_B / R_d. \tag{4}$$

$F_{max}$ occurs when $P_B$ is at its maximum allowable pressure which is the greatest pressure indicated on the pressure regulator, $P_{Bmax}$. Since F is inversely related to $R_d$, $F_{max}$ occurs at minimum $R_d$. Although $R_d$ is a variable, the design characteristics of the drain system give us a known value for $R_{dmin}$ because it occurs when the drain is completely open with no clogging or the like. Thus, $$F_{max} = P_{Bmax} / R_{dmin}. \tag{5}$$

Inserting (5) in (2) gives us $$P_{Fmax} = R_f * P_{Bmax} / R_{dmin}. \tag{6}$$

For any specific selected set of dimensions of the system, this expression gives the maximum pressure variation in the bladder due to flow variations.

To see the benefits derived from using different flow resistances of the feed conduit, equation (6) can be rearranged as follows:

$$R_f = R_{dmin} * P_{Fmax} / P_{Bmax}.$$

This tells us that the flow resistance of the feed conduit is equal to the minimum flow resistance of the drain conduit multiplied by the maximum pressure variation within the bladder divided by the maximum allowable pressure within the bladder.

When we know the minimum flow resistance of the drain conduit and we want to guarantee to the operator that the instrument can be used up to $P_{Bmax}$=200 mm of water with a guaranteed pressure variation $P_{Fmax}$ of not more than 10 mm of water, we see from equation (7) that $R_f = R_{dmin} * 10 / 200$. Thus, $R_f$ must be made 20 times smaller than $R_{dmin}$.

If the instrument dimensions are selected so that $R_f$ is still smaller than the value given in (7), the pressure variations are still smaller. This leads to the final inequality $$R_f < R_{dmin} * P_{Fmax} / P_{Bmax}. \tag{8}$$

In the foregoing example with a certain minimal drain flow resistance, a guaranteed maximum $P_{Bmax}$ of 200 and a guaranteed maximum pressure variation of 10, it is apparent from (8) that $R_f$ must be kept below 1/20 of $R_{dmin}$. Thus, the flow resistance of the feed conduit is kept smaller than the minimum flow resistance of the drain conduit multiplied by the maximum allowed pressure variation within the bladder divided by the maximum allowed pressure within the bladder.

In practice, the regulator is preferably positioned between about 20 cm above the bladder and about 50 cm below the bladder, but not higher than the minimum acceptable pressure in the bladder. If the regulator is below the bladder, it will be apparent that the distance below must be subtracted from, rather than added to, the pressure to which the regulator is set. The source 16 must, of course, be at sufficient height to provide the maximum anticipated or desired pressure required by the system.

The system including the shown pressure regulator 18 operates as follows:

First, the components are hooked up as shown in FIG. 1. Then flushing liquid flows from supply receptacle 16 through tube 17a into the pressure regulator of which the valve is open because of the loading by spring 35. Initially, the flushing liquid fills the chambers of the pressure regulator in housing parts 20 and 21. Advantageously, pushrod 38 is briefly manually forced inward by depressing knob 39 and the valve is kept in the open position for a short time so that air bubbles in the chambers can be quickly flushed out. The flushing liquid moves further through tube 17b and the feed duct 10 into the patient's bladder from which it is then drained as shown in FIG. 1. The valve in the pressure regulator 18 remains open until a specified pressure has been reached in the bladder. Thereafter, the flushing liquid increasingly forcefully pushes membrane 27 against spring 35, whereby membrane 27 deflects and the valve formed by valve aperture 31 and conical surface 32 closes. Because of the linear contact, good valve sealing is achieved and valve head 33 is centered, even if the membrane were offset.

When the liquid pressure in the chamber in body 20 forces the membrane to deflect until its return force balances that pressure, the valve closes and no more flushing liquid flows into the bladder. With further drainage through the drain line 11, 15, the bladder pressure drops and accordingly also drops the force deflecting the membrane 27. Again the return force of spring 35 overwhelms that of the liquid pressure deflecting membrane 27 and thus opens the valve, whereby liquid again flows in and the bladder pressure rises. Valve regulation begins again. In practice, the valve may not close completely at any time during flushing but may simply move to increase and decrease the gap between the valve and seat, depending on the flow rate.

At the beginning of flushing, the surgeon uses optics 5 of resectoscope 4 to observe the bladder inside and, by rotating adjustment screw 36, adjusts the bladder pressure until the bladder inside is seen to be in the desired open position. However, a preselected pressure setting may be used, at least initially, which is preset with adjustment screw 36 on the basis of prior experience.

The pressure regulator 18 must be held at a constant height above the bladder 1 while flushing is taking place. A suitable frame may be provided, or this regulator may be merely placed on the patient's abdomen.

The invention also applies to post-operation flushing. In that case a flushing catheter, for instance a balloon catheter with feed and drain ducts, connected to tubes 17b and 15 will be in the bladder in lieu of resectoscope 4. Such a device allows long-term flushing without risk, and without continuous monitoring of the bladder pressure by personnel. An alarm may be provided in the pressure regulator which responds upon excessive deflection of membrane 27 to alert the personnel.

The shown pressure regulator 18 may be varied in many ways within the scope of the invention. For instance with adequate miniaturization, it may be integrated into an instrument, illustratively the resectoscope 4 shown in FIG. 1, or into the alternatively discussed balloon catheter.

As regards the physical design features of FIG. 2, the inner works of the pressure regulator may be varied widely. The mechanical transmission between membrane 27 and valve head 33 may be different, for instance using toggle joints or the like. The adjustment of the spring force of membrane 27 may be different. Illustratively the air chamber in air chamber housing 19 may be sealed and be connected to a gas source generating regulated excess pressure on the gas side of the membrane 27 and setting the bladder pressure in this manner.

Prior to use, the inside of housing parts 20 and 21 must be fully sterilized because these inside surfaces come into contact with the flushing water. For that purpose the pressure regulator can be made sterilizable for re-use and for instance be autoclaved as a unit, or else it may be sterilized only by passing a disinfecting liquid through its liquid-filled chambers and the stubs 25a, 25b. The pushrod 38 is constantly forced inward during sterilization in order to keep the valve open.

Because of its simple and economical design, the entire pressure regulator may be made as a disposable item with its housing parts consisting of plastic.

In lieu of membrane 27, another type of pressure sensor may be used, for instance a piezoelectric one that illustratively controls the valve in electromotive manner.

As shown in the embodiment of FIG. 1, a flowmeter 45 is mounted in the feed tube 17a and monitors the flow and is connected to a system 46 which can be connected to emit an alarm when the flow falls below a given value.

Thereby the surgeon can be alerted immediately. Several reasons may be responsible for a pressure drop: supply receptacle 16 may be empty, or one of tubes 17a, 17b or 15 may be kinked and thereby blocked. However, most of the time there will be clogging of drain duct 11 by surgery residues, clogging, for example, holes 12 at the distal instrument end.

Otherwise the surgeon would notice the ebbing of the flushing flow not at all or much too late, the pressure regulator of the invention maintaining constant the pressure in the bladder and therefore the bladder condition being unchanging as observed by the surgeon, regardless of the magnitude of the flushing flow.

The flowmeter 45 may be a suitable system of the state of the art.

The flowmeter 45 moreover may be present elsewhere than at the site shown, for instance it may be integrated into the pressure regulator. Or it may be inserted into the drain tube 15, or be integrated into the instrument 4, that is into the feed duct 10 or the drain duct 11.

The application of the invention was described in relation to FIG. 1 for a constant-wash resectoscope 9 with both the feed duct 10 and the drain duct 11 being present in the same instrument. However, the pressure regulation of the invention also may be used with instruments with intermittent flushing and evincing only one duct with which both the supply and the discharge are carried out, the bladder being alternatingly filled and emptied. Again limitation of the maximum pressure is highly advantageous in such cases.

Again application is feasible when feed and drainage are carried out by means of separate instruments, illustratively a resectoscope similar to the instrument i shown in FIG. 1 being inserted through the urethra into the bladder and a supra-pubic catheter being inserted from the outside through a puncture duct into the bladder. This procedure has been increasingly resorted to lately and offers the advantage of making available ducts with large cross-sections in two instruments. Here again the feed may be provided in the manner of the invention with pressure regulation.

Lastly, the invention advantageously applies to catheters being used post-surgically for some time to wash the bladder. Again the pressure regulation of the invention is advantageous. The hook-ups may be carried out in the same manner as shown in FIG. 1 in relation to the instrument 9.

What is claimed is:

1. An apparatus for flushing the urinary bladder of a patient while maintaining the pressure within the bladder within a selected range of pressures below a maximum allowed pressure $P_{Bmax}$ and with maximum pressure variation $P_{Fmax}$ induced by flow variations, comprising the combination of instrument means insertable from the outside into the inside of a patient's bladder including a feed conduit (17b, 10) and a drain conduit (11, 15), each said conduit having an opening at a distal end thereof to be positioned within the bladder and an outside proximal end;

supply receptacle means (16) for providing flushing liquid under pressure;

a bladder pressure regulator (18) having an input connected to said supply receptacle means and an output connected to said proximal end of said feed conduit for providing flushing liquid at an adjustable constant pressure, said feed conduit between said regulator and the bladder having a constant flow resistance smaller than a minimum possible flow resistance of said drain conduit multiplied by said maximum pressure variation $P_{Fmax}$ and divided by said maximum allowable pressure $P_{Bmax}$; and means for mounting said regulator at a constant height relative to the bladder to be flushed, said constant height being not lower than a height for producing a minimum acceptable pressure within said bladder.

2. An apparatus according to claim 1 and further comprising flow controlling means in said drain conduit for controlling the drain flow.

3. An apparatus according to claim 2 wherein said flow controlling means is a suction pump.

4. An apparatus according to claim 1 wherein said regulator includes a spring-loaded membrane (27) with two sides, one of said sides being exposed to pressure from said flushing liquid and the other side being exposed to ambient air, a pressure-controlling valve, and means coupling the deflection of said membrane to said valve for mechanically driving said valve.

5. An apparatus according to claim 4 wherein said regulator includes a partition forming a separation between a first chamber communicating with said supply receptacle (16) and a second chamber communicating with the bladder (1), said partition being substantially parallel with said membrane and having a valve aperture therethrough, a valve rod (29) fixed to a side of said membrane (27) exposed to said flushing liquid and extending substantially perpendicularly from said membrane through said valve aperture (31) in said partition (24) and a valve head (33) carried by said rod on the opposite side of said partition (24) from said membrane and having a valve surface facing said membrane (27).

6. An apparatus according to claim 5 wherein said valve aperture (31) is circular and said valve surface (32) of the valve head (33) faces said membrane (27) and conically tapers relative to said valve rod (29), the smallest cross-section of said surface (32) being smaller than said valve aperture (31) and the largest cross-section being larger than the valve aperture (31).

7. An apparatus according to claim 6 wherein said regulator includes a spring (35) exerting a force against the side of said membrane (27) exposed to the air.

8. An apparatus according to claim 7 wherein said regulator includes an externally movable adjustment system (36) for adjusting the force exerted by said spring (35).

9. An apparatus according to claim 8 wherein said regulator includes a manually operable actuation means for moving said valve in the direction of opening, said actuation means including lost motion which is overcome before moving said valve.

10. An apparatus according to claim 9 wherein said regulator includes housing parts (19, 20, 21) of said pressure regulator (18) comprising plastic.

11. An apparatus according to claim 10 and including a flowmeter (45) in said feed line (17a, 17b, 10) between said supply receptacle means and said regulator.

12. An apparatus according to claim 10 and including a flowmeter (45) in said drain line (15, 11).

* * * * *